United States Patent
Peyman et al.

(10) Patent No.: US 6,384,043 B1
(45) Date of Patent: May 7, 2002

(54) METHODS OF ALLEVIATING PAIN SENSATIONS OF THE DENUDED EYE WITH OPIOID ANALGESICS

(75) Inventors: Gholam A. Peyman, 123 Walnut St., New Orleans, LA (US) 70118; Mohamad H. Rahimy, Metairie, LA (US)

(73) Assignee: Gholam A. Peyman, New Orleans, LA (US)

( * ) Notice: Subject to any disclaimer, the term of this patent is extended or adjusted under 35 U.S.C. 154(b) by 0 days.

(21) Appl. No.: 08/304,807

(22) Filed: Sep. 12, 1994

Related U.S. Application Data

(63) Continuation of application No. 08/012,035, filed on Feb. 1, 1993, now abandoned.

(51) Int. Cl.[7] ................... A61K 31/44; A61K 31/55
(52) U.S. Cl. ........................ 514/282; 514/171
(58) Field of Search ................. 514/282, 171

(56) References Cited

PUBLICATIONS

Kagan et al., Chemical Abstracts, vol. 72, No. 12, 59117h, 1970.*
Drago et al., Chemical Abstracts, vol. 101, No. 23, 204589n, 1984.*
Jiang et al., Chemical Abstracts, vol. 109, No. 4, 27659c, 1988.*
Chang et al., Chemical Abstracts, vol. 112, No. 9, 701996, 1990.*
Drago et al, "Ocular Opioids: Distribution and Function", Central and Peripheral Endorphins: Basic and Clinical Aspects, [Int. Meet. Ital. Soc. Endocrinology.], 1st, pp. 151–156, 1984.*
Kagan et al, "Spectrophotometric Determination of Pilocarpine, Ethyl Morphine and Novocaine Hydrochlorides in Eye Drops," Farm. Zh. (Kiev), vol. 24, No. 4, pp. 80–81, 1969 (translation from Ukrainian).*
Xinguo et al, "Research on the Quantitative Methods for Hydrocortisone Acetate and Deoxyadrenaline Hydrochloride in Compound Preparations," Acta Acadamiae Medicinae Shanghai, vol. 15, No. 1, pp. 77–80, 1988 (translation from Chinese).*
Chang et al, "The Inhibition of Prostaglandin E1–Induced Corneal Neovascularization by Steroid Eye Drops," Journal of the Formosan Medical Association, vol. 88, No. 7, pp. 707–711, 1989.*
Hargreaves and Jorist, "The Peripheral Analgesic Effects of Opioids," APS Journal 2(1): 51–59, 1993.
Stein, et al., "Analgesic Effect of Intraarticular Morphine After Arthroscopic Knee Surgery," New England Journal of Medicine 325:1123–1126, 1991.
Stein, "Peripheral Mechanisms of Opioid Analgesia," in Handbook of Experimental Pharmacology, vol. 104–1, Opioids (ed. by A. Herz et al., Springer–Verlag), 91–103, 1992.
Wood, "New Method of Treating Neuralgia by the Direct Application of Opiates to the Painful Points," Edinburgh Med. Surg. J., 82, 265–281 (1855).

* cited by examiner

Primary Examiner—William R. A. Jarvis
(74) Attorney, Agent, or Firm—Woodcock Washburn LLP

(57) ABSTRACT

A method of alleviating pain sensations in a denuded eye comprising the step of applying topically to the eye an analgesic solution with the analgesic solution comprising an opioid analgesic is disclosed.

16 Claims, 1 Drawing Sheet

METHODS OF ALLEVIATING PAIN SENSATIONS OF THE DENUDED EYE WITH OPIOID ANALGESICS

This is a continuation of application Ser. No. 08/012,035 filed on Feb. 1, 1993 now abandoned.

BACKGROUND OF THE INVENTION

This invention relates to ophthalmic analgesic agents and in particular to topical ophthalmic agents which are generally used for alleviation of pain sensation in the cornea and conjunctiva due to disease or injury.

Currently, local ophthalmic analgesia is achieved using various anesthetic agents. The anesthetic agents used include topical application of tetracaine hydrochloride, procaine hydrochloride, benoxinate hydrochloride, and proparacaine hydrochloride. Tetracaine, a derivative of para-aminobenzoic acid, is generally applied as a 2.5% solution or by ointment. Procaine is available in concentrations of 1% solution, 2% solution, or 10% solution. Benoxinate, a benzoic acid and related to procaine, is used in a 0.4% solution prior to intraocular pressure measurement. Alcaine, a benzoate, is available in a 0.5% solution. Another drug which has been used as a local ophthalmic anesthetic is cocaine, which is one of the first agents discovered and has been used since the beginning of this century. Extensive pharmacological studies have shown that these drugs when used at therapeutic doses of 5,000 to 20,000 ug/ml exhibit an anesthetic property by completely blocking the neuronal conduction.

Unfortunately, repeated or prolonged application of topical ophthalmic anesthetics has been shown to exert deleterious effects on corneal epithelium, lacrimal glands, mucous production, and cell motility. Furthermore, recent studies have demonstrated that even a single dose of topical anesthetic can cause severe toxicity to the corneal epithelium. Major toxic effects of these drugs include: 1) inhibition of corneal regeneration or re-epithelialization that may result in sloughing of the corneal epithelium, which then exposes the corneal stroma to subsequent destructive effects of pathogenic microorganisms, causing corneal ulcers; 2) alteration in lacrimation and mucous adherence causing decrease in stability of the precorneal tear film; 3) increase in corneal permeability and swelling which results in loss of corneal transparency; and 4) altering corneal epithelial cytoskeletal elements (actin, myosin), which causes disruption of cell motility. Other adverse effects include allergic dermatitis which is seen in sensitive patients. Thus, the profound anesthetic property exhibited by these drugs severely limits their application as topical ophthalmic analgesics. In fact, following application of these topical anesthetics the loss of corneal sensitivity is so profound that some patients inadvertently injure their corneas without being aware of the extent of the self-injury. From the therapeutic standpoint, the outcome of such therapy seems as painful as giving no drug at all. Clearly, it seems that local analgesia can not be achieved by these anesthetics without impairing the normal function of the eye. Collectively, these inherent problems have limited the use of topical ophthalmic anesthetics for pain relief following corneal abrasion and/or injury.

The need for a truly useful ophthalmic analgesic is even more pressing in that numerous ocular conditions, diseases, and injuries would be treated if a safer formulation was available. An ideal formulation should be composed of an effective analgesic which does not cause any adverse effects or permanent damage to ocular structures. The ideal formulation could be prescribed by physicians for the following ocular conditions: 1) any injury to the eye causing damage to the corneal epithelium and conjunctiva, such as traumatic corneal abrasion, penetration, perforation, acid and alkali burn, or any other chemical burn; 2) any disease causing dry eye syndrome and the subsequent loss of localized or diffused corneal-epithelial cell damages, such as keratoconjunctivitis scica, vitamin A deficiency, abnormalities of the eye lids and eye lashes; 3) eye diseases causing cicatricial changes of the conjunctiva and cornea, such as traucoma; 4) viral infection affecting corneal epithelium and/or stroma, such as Herpes viruses and others; 5) bacterial and fungal infections causing corneal ulcers; and 6) any disease affecting lacrimal glands causing lower tear production. These medications could also permit removal of foreign bodies from the conjunctiva, cornea, and those which are dislodged under the superior lid.

The application of this ideal formulation or analgesic agent may eliminate the unnecessary use of local anesthetics or general anesthesia for the examination of sensitive eyes in some patients. Furthermore, the use of this ideal formulation could facilitate general ophthalmic examinations, such as the use of fundus contact lenses for evaluation of the background of the eye or the angle of the anterior chamber. It could also be used prior to the measurement of intraocular pressure. Additionally, an ideal formulation of an ophthalmic analgesic preparation must not irritate or cause any permanent damage to the ocular structures.

For all these reasons, development of a safe, effective topical fommulation for ophthalmic analgesic is warranted. If a topical formulation exhibits an effective analgesia without damaging the corneal epithelium and without having a profound anesthetic property, it may permit normal regrowth of the epithelial cells without any delay over the denuded areas of the cornea. Such a local analgesic can be used for temporary relief of pains in patients having corneal and conjunctival diseases or injuries, without experiencing the deleterious toxic effects of currently used local anesthetics.

SUMMARY OF THE INVENTION

An ophthalmic formulation for topical treatment of an eye comprises an opioid analgesic solution. The ophthalmic formulation comprises an aqueous solution of an opiate agonist, such as morphine, in the range of about 0.01 to about 5 mg/ml (0.01–0.5% by weight), having a physiologic pH close to 7.4 and osmolarity of about 300 milliosmol. The preferred concentration of the opiate agonist in the ophthalmic formulation is in the range of about 0.5 to about 0.8 mg/ml.

Accordingly, it is an object of the invention to provide a topical ophthalmic analgesic formulation which does not impair or damage the corneal epithelial cells or other ocular structures.

It is a further object of the present invention to provide a local ophthalmic analgesic formulation which does not exhibit a profound anesthetic property.

It is a still further object of the present invention to provide a local ophthalmic analgesic formulation for use in treating various corneal and conjunctival injuries and diseases.

It is another object of the present invention to provide a local ophthalmic analgesic formulation to be used prior to the measurement of intraocular pressure.

These and other objects and advantages of the present invention will become apparent to those skilled in the art after considering the following detailed specification in conjunction with the accompanying drawing, wherein:

DETAILED DESCRIPTION OF THE PREFERRED EMBODIMENTS

Figure 1:
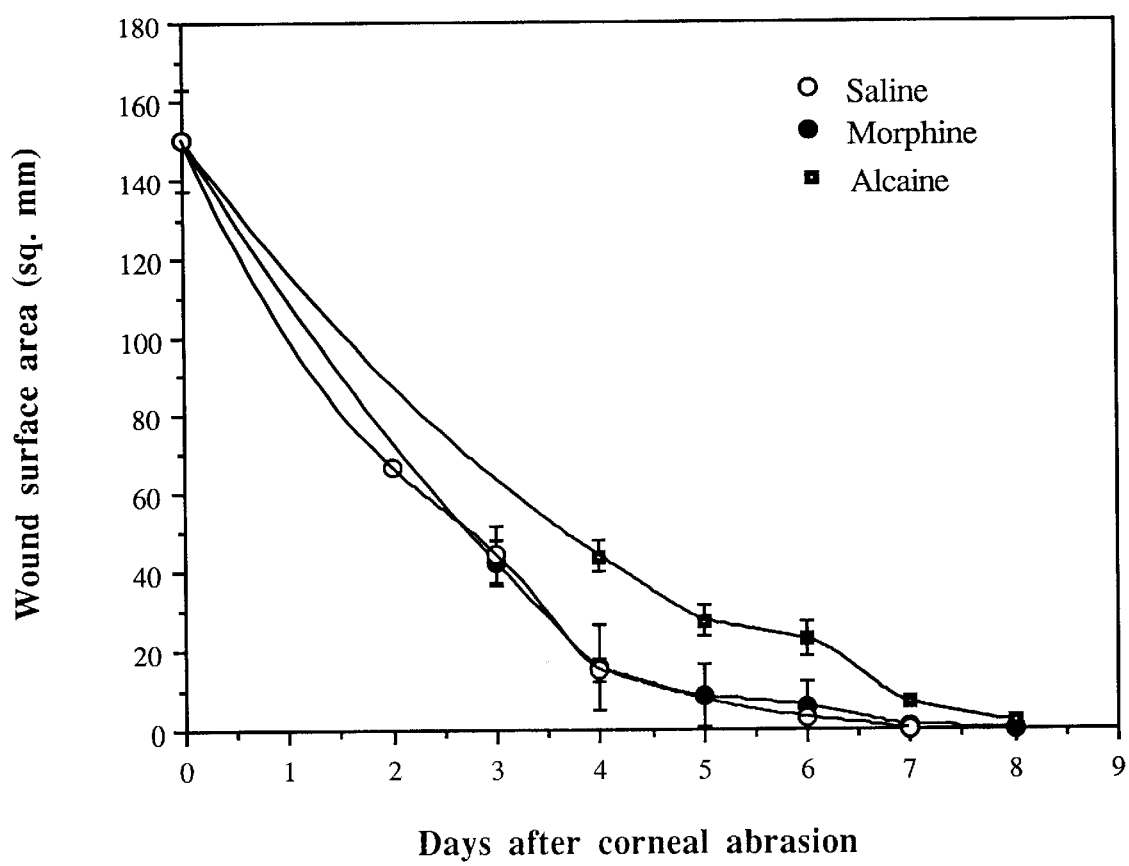
FIG. 1 is a graph of the relationship between wound surface area healing versus days after corneal abrasion for three different treatment groups.

As described above, ophthalmic anesthetics can provide corneal and conjunctival analgesia, but their observed toxicities at therapeutic levels (0.5% to 2% by volume) have limited their use as topical analgesics.

As a result of recent investigations, the applicants herein have found that topical application of opiates, such as morphine sulphate, at low concentration results in effective analgesia in patients with corneal abrasion or after a surgical refractive procedure as early as 10 minutes following application. Furthermore, it has been found that this analgesic formulation does not exhibit any adverse effects, as examined in an abrasion and healing model, on corneal epithelial cells regeneration, migration, and permeability. To our knowledge, the effects of ophthalmic formulations of containing morphine or other opiates as a topical or local analgesic medication for a corneal and conjunctival pain therapy have never been described. The present invention is based upon the above findings.

In the past, the use of morphine or other opiates as analgesic agents have been by systemic routes including oral, subcutaneous (SC), intramuscular (IM) or intravenous administration (IV). The analgesic response experienced following the use of opiates is believed to be the result of opioid receptor activation in the central nervous system. This theory that opiates produce their effects by interacting with receptors developed from observations that specific structural and stereochemical requirements are necessary for their analgesic action. Recently, the existence of multiple opioid receptor types and subtypes have been suggested based on the relationship between the molecular structure of opiate drugs and their analgesic effect. Thus, the discovery of opiate receptors in the central nervous system reinforced the search for identification of endogenous opioids, as well as demonstration of opiate receptors in the peripheral nerve terminals (Stein et al., J. Pharmacol. Exp. Ther. 248,1269–75 (1989)). Several recent studies have demonstrated that opiate agonists exhibit peripheral analgesic effects in inflamed tissue of animals (Joris et al., Anesth. Analg. 66,1277–1281 (1987); Stein et al., J. Neurosci. 10,1292–1298 (1990)), and that the antinociceptive effects of opiate mu- and kapa agonists are enhanced by peripheral opioid receptor-specific mechanism (Stein et al., Eur. J. Pharmacol. 155,255–264 (1988)). Furthermore, in a double-blind, clinical trial study, the analgesic efficacy of a low dose, aqueous morphine solution was investigated. When morphine was applied locally inside the joints following knee surgery, it significantly reduced pain scores, more likely due to local activation of opioid receptors that reached maximal effect in 3 to 6 hours (Stein et al., New Engl. J. Med. 325,1123–1126 (1991)).

The only indication that opiates may have receptors and perhaps a physiologic role in the surface structures of the eye comes from a Fanciullacci et al. observation (Eur. J. Pharmacol. 61,319–320 (1980)). Fanciullacci et al have shown that when an opiate antagonist, such as naloxone, is applied topically to one eye of a morphine-dependent subject (a conjunctival-test model for morphine addiction), it causes pupillary dilation in the same eye. Numerous other studies have examined the effects of opiates on pupillary diameter following IM, IV, SC, or oral administration. Miosis or pupillary constriction is a consistent effect of opiates and since there is an excellent agreement between the potency of analgesics in producing miosis and generalized analgesia, the miosis phenomenon has been utilized as a bioassay test for studying the time course and relative potency of opiate analgesic drugs in man. However, the effects of an ophthalmic formulation of morphine or other opiates as a topical/local analgesic medication for the corneal and conjunctival therapy have not been reported.

The primary component of the analgesic formulation will be an opioid drug of endogenous or synthetic origin. The ophthalmic solution can be formulated to include one or more drugs at therapeutically effective concentrations to be applied topically. Any pharmacologically active opioid with an analgesic property may be used in the formulation. The drug may be an endogenous opioid or a synthetic analgesic from the agonist, partial agonist, or agonist-antagonist group, preferably with less addictive or abuse potential. Also, antiprostaglandins and antiprostacyclins may be employed, in combination with opioids, in the topical analgesic formulation. Desirably, the drug will be sufficiently soluble in the physiological solution to be formulated at a therapeutically effective analgesic dose.

Drugs of particular interest include opiate agonists, such as buprenorphine, codeine, dextrorphan, dynorphins, endorphins, fentanyl, hydrocodone, hydromorphone, ketocyclazocine, levorphanol, meperidine, methadone, normorphine, oxymorphone, profadol, propoxyphene, and propiram; and agonist-antagonists, such as butorphanol, cyclazocine, ethylketocyclazocine, diprenorphine, nalbuphine, nalorphine, normetazocine, and pentazocine.

Other drugs of interest include anti-cyclooxygenases, such as aspirin-like anti-inflammatory agents including: aspirin, indomethacin, ibuprofen, fenoprofen, flurbiprofen, phenylbutazone, ketorolac tromethamine, sulindac, apazone, mefenamic, tolemtin, naproxen, piroxicam, suprofen, voltaren, and zomepirac; and steroids, particularly anti-inflammatory drugs, such as cortisone (or its acetate salt), hydrocortisone (or its acetate, cypionate, succinate, sodium phosphate salts), prednisone, prednisolone (or its acetate, tebutate, sodium phosphate salts), 6 alpha-methyl-prednisolone (or its acetate, succinate salts), fludrocortisone, fluorometholone, beclomethasone, betamethasone (or its acetate, benzoate, dipropionate, valerate, sodium phosphate salts), dexamethasone (or its acetate, sodium phosphate salt), medrysone, paramthasone (or its acetate salt), and triamcinolone (or its acetonide, diacetate, hexacetonide salts).

Other pharmacologic agents may be employed in the formulation for a variety of purposes. In addition to the active ingredient, diluents, buffering agents and preservatives may be employed. The water soluble preservatives include benzalkonium chloride, antioxidants, such as ascorbic acid, sodium bisulfite, parabens, benzyl alcohol and with or without essential vitamins. The essential vitamins include vitamin A and/or vitamin E. The formulation may contain sodium chloride, glucose, calcium, magnesium, glycerin, hydrochloric acid and/or sodium hydroxide to adjust osmolarity and pH. These agents may be added in amounts of from 0.001 to 5%. The pH of the formulation will be maintained between 6 to 8, preferably in the range of about 7 to about 7.4.

The formulation may be supplied in a single use plastic bag or regular ophthalmic drug bottles or may be in the form of an ointment preparation.

The following describes the preparation of a preferred embodiment of a topical ophthalmic analgesic formulation. An amount of morphine sulphate was dissolved in a normal saline solution to form a concentrated stock solution. Then, appropriate dilutions were made from the stock solution in order to prepare a morphine concentration of 0.5 milligram/millileter (0.05% by volume). This concentration of analgesic preparation was chosen because previous observations had shown that this dose of morphine was sufficient to cause suppression of pain pressure in animals and humans. The pH of the solution was adjusted to 7.2 with addition of a hydrochloric acid and/or a sodium hydroxide solution. The osmolarity was also adjusted to 300 milliosmol with addition of sucrose or glucose. Immediately before each study, the analgesic preparation was sterilized by filtering through a 0.2 micrometer filter into a sterilized test tube. The solution was withdrawn into a syringe and used as needed. The stability results indicated that there was no detectable changes in color or amounts of morphine degradation when the solution was protected from light and stored at −20° C. or 4° C. for over a month.

The following describes analgesic tests which were performed on patients following topical application of the prepared and previously described topical ophthalmic analgesic formulation. This study was designed to examine the analgesic efficacy of the morphine formulation, the time to exhibit response, and dose proportionality in subjects with corneal abrasion or after a refractive procedure, when the drug is applied topically to the eye. Five patients were selected to participate in this study. In all cases, three measurements were made in the following fashion: First, a baseline response (corneal sensitivity) was established by determining the response of the patient eye to a standard pain pressure using a Cochet Bonnet Aesthesiometer instrument and without applying any drug. Measurements were made by beginning with the nylon monofilament (0.12 mm diameter) fully extended. The tip was applied perpendicularly to the corneal surface and gently pressed until the fiber's first visible bending. The length of the fiber was gradually decreased until a blink reflex and/or a verbal pain response were observed. The length was then recorded in units of mm. Second, a saline solution (2 drops) were instilled in the eye and at 10 and 20 minutes later the response of the patient's cornea to pain pressure was determined as described above. These repeated measurements served as a placebo effect for comparison purposes. Finally, 2 drops of the morphine formulation were instilled in the eye and the analgesic effect on the cornea was assessed. It is important to point out the clinician responsible for evaluating the ophthalmic solutions was not informed of the nature of the drugs being tested. Results of these tests are shown in the following table designated as Table 1.

TABLE 1

Analgesic Effects of Morphine (0.5 mg/ml) on
Corneal Sensitivity of Patients
Expressed as Pressures in grm/sq. mm

| Drug | Dose (drops) | Time after topical drug treatment | | |
|---|---|---|---|---|
| | | 0 | 10 min | 20 min |
| None | Baseline | 1.95 ± 0.20 | — | — |
| Saline | 2 (0.9% by volume) | | 1.73 ± 0.42 | 1.68 ± 0.72 |
| Morphine | 2 (0.5% by volume) | | 7.69 ± 2.16 | 9.84 ± 1.00 |

The values in the above Table 1 are the mean pressures±SEM (standard error of the mean). Again, an Aesthesiometer, based upon the principle of pressure transmitted axially by a nylon monofilament of known diameter but of variable length for a given bending stress, was applied to the corneal surface. By decreasing the length and exerting slight pressure on the tip of the monofilament, the patient reacts to the pain pressure. The distance, in millimeters (mm) of the nylon monofilament is recorded and then converted to pressure in gram/square millimeter.

As shown in Table 1, application of saline eye drops had no analgesic effects as expected. The analgesic response (corneal sensitivity) to saline solution at 10 and 20 min. was very similar to the baseline response. On the contrary, topical application of two drops of the morphine formulation (0.05% by weight solution) exhibited a dramatic analgesic effect as early as 10 minutes after administration. The magnitude of pain suppression by the morphine solution was such that much greater pressures in gram/sq.mm were required to obtain a corneal sensitivity response. As such, the present morphine formulation exhibited an analgesic efficacy of 4.3 and 5.5-fold greater than the baseline or saline responses at 10 and 20 minutes, respectively. Interestingly, the analgesic response observed at 20 minute is greater than the response observed at 10 minute, indicative of time-dependent analgesic effect by morphine. It seems that the maximal analgesic effect of the morphine formulation may not occur until after 20 minutes following topical application.

The following describes toxicity tests which were performed on animals following topical application of the prepared and previously described topical ophthalmic analgesic formulation. Healthy pigmented rabbits weighing about 1.5–2.2 kg were anesthetized and then corneal epithelial cells were scraped and removed using a blade under direct view of a microscope. The basal lamina was left intact while thorough de-epithelialization was performed and confirmed by staining the surface of the cornea with 1% fluorescein. All eyes were thoroughly washed with saline and randomly divided into three treatment groups as follows: 1) saline solution (control), 2) morphine formulation, and 3) proparacaine HCl (positive control). Eyes in each group were instilled with two drops of the corresponding solution at 4 hourly intervals for 6 consecutive days. Wound healing (corneal re-epithelialization) was assessed on days 2, 3, 4, 5, 6, 7, and 8 following corneal abrasion using fluorescein staining with Fluor-I-Strip, and epithelial regeneration and migration were monitored by clinical examinations as well as wound surface area measurements. The results of these tests are shown in FIG. 1 and Table 2.

In FIG. 1, the line with open circles indicates saline effects on corneal re-epithelialization, the line with closed circles indicate when morphine (0.5% by volume) was applied to the cornea, and the line with closed triangles indicates when Alcaine (0.5% by volume) was applied.

As show in FIG. 1 and Table 2, repeated topical application of the morphine formulation had no adverse effect on the corneal epithelial cell regeneration and migration. In fact, rates of wound closure were similar in both saline and morphine treated groups. Eyes treated with the morphine formulation began to show epithelial regeneration on the second day and complete regeneration by 4 days following corneal abrasion. The progression of wound closure was normal since by 4 days (1 eye), 5 days (3 eyes), and 7 days (5 eyes) completed regeneration. Only 1 eye did not show complete wound closure due to infection. On the contrary, repeated application of Alcaine significantly prevented regeneration of the corneal epithelial cells. Eyes treated with the Alcaine formulation began to show corneal regeneration on the third day and complete wound healing by 8 days following corneal abrasion. The time-course study showed that only 2 eyes out of 6 in the Alcaine group had completed regeneration of the corneal epithelium by 8 days, the last time point observed. Interestingly, only 1 eye of the remaining 4 eyes with incomplete epithelial regeneration developed infection in the Alcaine treated group.

TABLE 2

Progression of Corneal Epithelial Regeneration Following Mechanical Epithelial Cells Removal

| Drug | Days after drug treatment | | | | | | | |
|---|---|---|---|---|---|---|---|---|
| | 1 | 2 | 3 | 4 | 5 | 6 | 7 | 8 |
| Saline 2 drops | 0/4 | 0/4 | 0/4 | 1/4 | 1/4 | 2/4 | 2/4 | — |
| Morphine 2 drops (0.5% by volume) | 0/6 | 0/6 | 0/6 | 1/6 | 3/6 | 4/6 | 5/6 | 5/6 |
| Alcaine 2 drops (0.5% by volume) | 0/6 | 0/6 | 0/6 | 0/6 | 0/6 | 0/6 | 0/6 | 2/6 |

In Table 2 above, the first number represents the number of animals which exhibited complete healing of the cornea and the second number represents the total number of animals per group. For example, 0/4 under day 1 for Saline represents zero animals exhibited complete healing of the cornea out of a total of four animals for this group.

There has thus been shown and described a novel topical ophthalmic analgesic formulation which fulfills all of the objects and advantages sought therefor. It will be apparent to those skilled in the art, however, that many changes, modifications, variations, and other uses and applications of the subject topical ophthalmic analgesic formulation are possible and contemplated. All such changes, modifications, variations, and other uses and applications which do not depart from the spirit and scope of this invention are deemed to be covered by the invention, which is limited only by the claims which follow.

What is claimed is:

1. A method of alleviating pain sensations in a denuded eye comprising the step of applying topically to the denuded eye an analgesic solution, said analgesic solution comprising an opioid analgesic in an effective amount to allevate pain sensations in the denuded eye.

2. The method of alleviating pain sensations in the eye of claim 1 wherein the analgesic solution comprising the opioid analgesic is in the range of about 0.5 mg/ml to about 0.8 mg/ml, in a solution having a pH in the range of about 7.0 to about 7.4, and an osmolarity of about 300 milliosmol.

3. A method of alleviating pain sensations in a denuded eye comprising the step of applying topically to the denuded eye an opioid analgesic, in the range of about 0.01 mg/ml to about 5 mg/ml, in a solution having a pH in the range of about 6.0 to about 8.0 in an effective amount to topically treat the denuded eye.

4. The method of claim 3 wherein the preferred range of the opioid analgesic is about 0.5 mg/ml to about 0.8 mg/ml.

5. The method of claim 3 wherein the preferred range of pH of the solution is in the range of about 7.0 to about 7.4.

6. The method of clain 3 wherein the opioid analgesic has an osmolarity of about 300 milliosmol.

7. The method of claim 3 wherein the solution contains anti-inflammatory steroidal.

8. The method of claim 3 wherein the solution contains an effective amount of buffering agent.

9. The method of claim 3 wherein the solution contains an effective amount of preservative.

10. The method of claim 3 wherein the solution contains an effective amount of antioxidant.

11. The method of claim 10 wherein the antioxidant is ascorbic acid.

12. The method of claim 3 wherein the solution contains an effective amount of essential vitamin.

13. The method of claim 12 wherein the essential vitamin is vitamin A.

14. The method of claim 12 wherein the essential vitamin is vitamin E.

15. The method of claim 3 wherein the opioid analgesic comprises morphine and salts thereof.

16. The method of claim 3 wherein the opioid analgesic comprises a derivative of morphine and salts thereof.

* * * * *